US009872681B2

(12) United States Patent
Miller et al.

(10) Patent No.: US 9,872,681 B2
(45) Date of Patent: *Jan. 23, 2018

(54) METHOD AND APPARATUS FOR DELIVERING A SHAPE MEMORY ARTICLE TO A SURGICAL SITE

(71) Applicant: OsteoMed LLC, Addison, TX (US)

(72) Inventors: Alan B. Miller, Jamison, PA (US); Shawn T. Huxel, Lawrenceville, NJ (US); Richard Thomas Briganti, Philadelphia, PA (US)

(73) Assignee: OsteoMed LLC, Addison, TX (US)

( * ) Notice: Subject to any disclaimer, the term of this patent is extended or adjusted under 35 U.S.C. 154(b) by 970 days.

This patent is subject to a terminal disclaimer.

(21) Appl. No.: 14/026,665

(22) Filed: Sep. 13, 2013

(65) Prior Publication Data

US 2014/0034702 A1 Feb. 6, 2014

Related U.S. Application Data

(63) Continuation of application No. 12/708,973, filed on Feb. 19, 2010, now Pat. No. 8,596,514.

(Continued)

(51) Int. Cl.
*A61B 17/068* (2006.01)
*A61B 17/064* (2006.01)
(Continued)

(52) U.S. Cl.
CPC ........ *A61B 17/068* (2013.01); *A61B 17/0642* (2013.01); *A61B 17/0682* (2013.01);
(Continued)

(58) Field of Classification Search
CPC ...... A61B 17/0682; A61B 2017/00867; A61B 17/0642; A61B 17/068
(Continued)

(56) References Cited

U.S. PATENT DOCUMENTS 1,106,241 A    8/1914    Richardson
4,438,769 A    3/1984    Pratt et al.
(Continued)

FOREIGN PATENT DOCUMENTS

EP    0826340 A2    3/1998
EP    1870042 A1    12/2007
(Continued)

OTHER PUBLICATIONS

International Search Report dated Apr. 7, 2010 for PCT/US2010/024728 and Written Opinion of the International Searching Authority.

(Continued)

*Primary Examiner* — Michelle Lopez
(74) *Attorney, Agent, or Firm* — Norton Rose Fulbright US LLP

(57) ABSTRACT

The invention pertains to a method and apparatus for delivering an article formed of a shape memory alloy to a surgical implantation site. The apparatus may include a body having a passage for receiving the proximal portion of the shape memory article, the passage being shaped to substantially prevent the shape memory article from deforming in accordance with its shape memory properties when the proximal portion of the shape memory article is positioned in the passage. An exemplary involves placing the distal portions of legs of a staple in at least one passage in a constraining device that substantially constrains the legs from deforming; and placing the proximal portions of the legs of the staple in at least one passage in an apparatus that, independently of the constraining device, substantially prevents the legs from deforming.

23 Claims, 14 Drawing Sheets

Related U.S. Application Data

(60) Provisional application No. 61/161,604, filed on Mar. 19, 2009.

(51) Int. Cl.
*A61B 17/10* (2006.01)
*A61B 17/00* (2006.01)

(52) U.S. Cl.
CPC .......... *A61B 17/10* (2013.01); *A61B 17/0644* (2013.01); *A61B 2017/0023* (2013.01); *A61B 2017/00867* (2013.01); *A61B 2017/0645* (2013.01)

(58) Field of Classification Search
USPC ................ 227/175.1, 176.1, 181.1; 606/219; 411/904
See application file for complete search history.

(56) References Cited

U.S. PATENT DOCUMENTS

| | | | |
|---|---|---|---|
| 5,353,929 A | 10/1994 | Foster | |
| 5,379,895 A | 1/1995 | Foslien | |
| 5,392,917 A | 2/1995 | Alpern et al. | |
| 5,715,987 A | 2/1998 | Kelley et al. | |
| 6,030,410 A | 2/2000 | Zurbrugg | |
| 6,197,032 B1 | 3/2001 | Lawes et al. | |
| 6,685,708 B2 | 2/2004 | Monassevitch et al. | |
| 6,939,358 B2 | 9/2005 | Palacios et al. | |
| 7,028,878 B2 | 4/2006 | Bauer | |
| 7,533,790 B1 | 5/2009 | Knodel et al. | |
| 7,699,203 B2 | 4/2010 | McBride et al. | |
| 7,753,250 B2 | 7/2010 | Clauson et al. | |
| D675,734 S | 2/2013 | Cheney et al. | |
| 8,393,517 B2 | 3/2013 | Milo | |
| 8,596,514 B2 * | 12/2013 | Miller | A61B 17/0642 128/898 |
| 2005/0096660 A1 | 5/2005 | Allen | |
| 2010/0100138 A1 | 4/2010 | Reynolds et al. | |
| 2010/0237128 A1 | 9/2010 | Miller et al. | |
| 2012/0228355 A1 | 9/2012 | Combrowski et al. | |
| 2013/0030437 A1 | 1/2013 | Fox | |

FOREIGN PATENT DOCUMENTS

| | | |
|---|---|---|
| FR | 2716105 A1 | 8/1995 |
| FR | 2758252 A1 | 7/1998 |
| WO | WO2008/129061 A1 | 10/2008 |

OTHER PUBLICATIONS

Extremity Reconstructive Surgery Catalog, Integra LifeSciences Corporation, http://integralife.com/eCatalogs/Extremity-Reconstruction/Extremity-Reconstruction-Catalog-NS1725-01-08.pdf, 2008, 87 pages.

Memory™ Staple Surgical Technique: Controlled Compression for Fusion, DePuy, http://www.pei.ie/PEI/media/PEI- media/PDFs/PDFs_Ortho/PDFs_Ortho_Products/PDFs_Ortho_Products_DePuy/memory_staple_surgical_technique.pdf, 2006, 16 pages.

Charlotte® Compression Staple Surgical Technique; Wright Medical Technology, http://www.wmtemedia.com/ProductFiles/Files/PDFs/011184_EN_LR_LE.pdf, 2010, 8 pages.

* cited by examiner

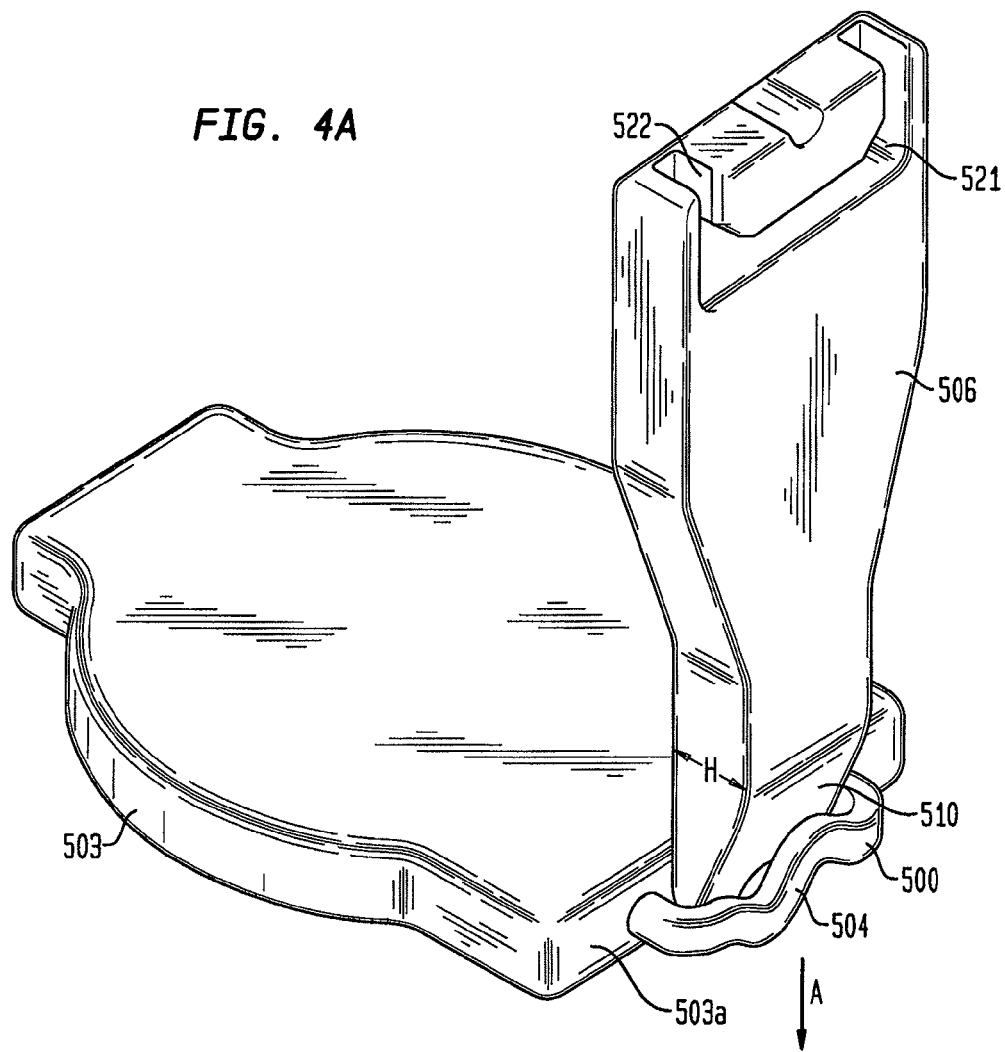

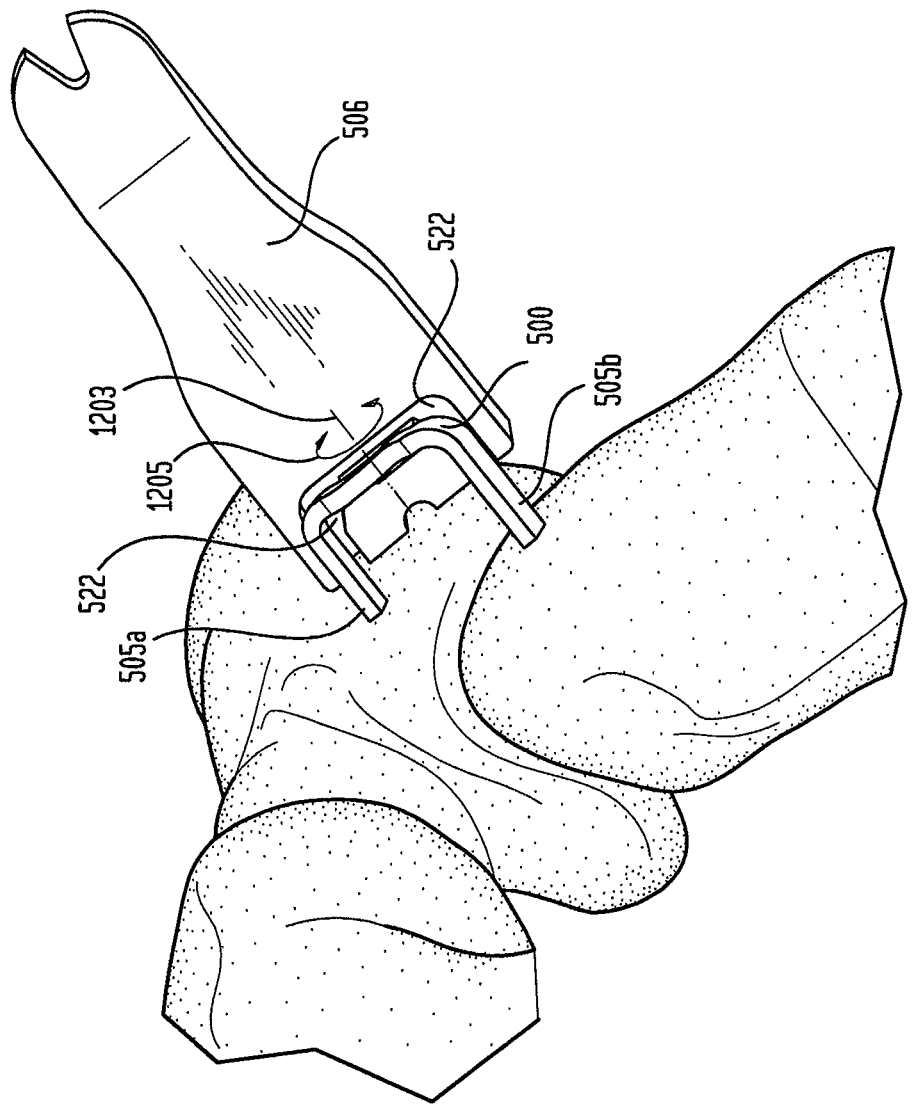

METHOD AND APPARATUS FOR DELIVERING A SHAPE MEMORY ARTICLE TO A SURGICAL SITE

CROSS-REFERENCE TO RELATED APPLICATIONS

This application is a continuation of U.S. application Ser. No. 12/708,973, filed on Feb. 19, 2010, which claims priority to U.S. Provisional Patent Application No. 61/161,604, filed Mar. 19, 2009, the disclosure of each of which is hereby incorporated herein by reference.

BACKGROUND OF THE INVENTION

Shape memory articles (SMAs), comprised, for instance, substantially of NiTinol alloy, are used in many surgical applications, including use as staples for re-attaching tissue or bone. Usually, external heat is applied to the shape memory article in order to transition it from a first shape in a martensitic, softer, morphology to a second shape in an austenitic, stiffer, morphology.

When a patient suffers an injury in which tissue or bone must be reapproximated, reattached, or fused, the injury often must be repaired by surgically securing the tissue or bone together with internal fixation devices such as plates, screws, pins, or staples. These devices are often rigid and have geometric features that enable them to reapproximate, reattach, or fuse tissues. Examples of these features include threads, grooves, overall shape of the device, and other features that provide attachment or support. Any undesired deformation of these devices could lead to increased amounts of strain and ultimate failure of the device.

Since the late 1980's, NiTinol, a Nickel-Titanium alloy, has been increasingly utilized in a variety of medical devices and, in some cases, has become one of the materials of choice for many designers and engineers. From surgical devices to endoluminal stents and other prostheses, the thermo-mechanical characteristics of the material and its biocompatibility have allowed its use across many medical and surgical specialties both for diagnostic and therapeutic applications.

The shape memory effect results from a reversible crystalline phase change known as martensitic transformation. Shape memory alloys can display various types of shape memory. The type of shape memory that has probably found the most use in commercial applications is commonly referred to as one-way shape memory. In one-way shape memory, an article formed of a shape memory alloy in an original shape can be substantially plastically deformed into a shape while it is in the soft, martensitic phase and it will remain in that shape, (hereinafter the deformed shape). Then, upon heating above a first temperature, the material returns to its original (prior to deformation) shape while transitioning from the soft, martensitic phase to a much stiffer austenitic phase. It should be noted that, while the article is much stiffer in the austenitic phase, it usually is still somewhat deformable, but primarily elastically, as opposed to plastically, deformable. Upon cooling below a second temperature that is below the first temperature, the material transitions back to the softer, martensitic phase, but maintains the shape it took during the transformation to the austenitic phase (i.e., its original shape) until it is acted upon by an external force or stress. Because the material is less stiff (i.e., more pliable) in its martensitic phase, it is much easier to bend (back to the deformed shape or any other shape) and it will maintain that new shape up to and until it is heated once more above its transformation temperature.

The strength and transition temperatures of SMAs can be greatly varied by changing the exact composition of the alloy and/or the thermal history of the article.

The use of shape memory staples in surgical skeletal repair enables a staple to be installed in bone or tissue in one shape while in its martensitic phase and then be heated to cause it to transition to the much stiffer austenitic phase while shifting to another shape that, for instance, draws the tissue or bone closer together. Many medical applications use SMAs having a transition temperature for complete martensitic to austentitic transformation of about 55° C. However, other medical applications utilize alloys having a complete transition temperature at about human body temperature of 37° C.

While metallic staples have long been used for static fixation, the use of shape memory alloys (SMAs) in staples and their attendant ability to apply dynamic continuous compression is a major advancement in tissue and bone uniting that potentially improves the healing process in connection with the repair, fusing, and remodeling of damaged tissue. These SMA staples are smaller and less bulky than other fixation devices, such as plates, screws, and nails. They permit smaller incisions, which cause less trauma and scarring and lead to faster post-operative recovery. Also, since fewer holes need to be drilled and no screws are needed, more rapid surgical procedures are possible.

The shape memory properties described hereinabove are sometimes referred to as superelasticity, particularly when the transition from martensitic phase to austenitic phase occurs at lower temperatures, such as room temperature or below. The terminology is not consistent in the art. In this specification, we shall simply use the term shape memory generically as encompassing superelasticity.

FIG. 1 is a graph showing a dynamic scanning calorimetry (DSC) for one particular NiTinol composition. DSC is useful for determining the temperatures at which various substances undergo phase changes. In the case of NiTinol or other SMA articles, DSC is utilized to understand the temperatures required for transitioning from the martensitic phase to the austenitic phase and back again. DSC measures the heat flow necessary to maintain the article at a certain temperature. The bottom portion of the scan represents the state of the article at −50° C. as it is subjected to increasing temperature over time. This graph shows a stable structure (martensitic morphology) during temperatures up to an austentitic start temperature ($A_s$) of approximately 29° C., where phase transformation to the austenitic phase theoretically begins. As demonstrated by this scan and the change in heat flow, the metal is fully transformed into its stiff, austenitic phase at the austentitic finish temperature ($A_f$) of approximately 50° C. The top portion of this scan represents cooling of the austenitic NiTinol article starting at 100° C. Note that the martensitic phase recovery theoretically begins at the martensitic start temperature (Ms) of approximately 19° C. and is complete at the martensitic finish temperature of approximately 0° C. This is only an example of one form of NiTinol shape memory alloy. Other transition temperatures are achievable with different chemical compositions and thermo-mechanical treatments.

Using the exemplary material above, one can see that the device is geometrically stable in its martensitic phase up to room temperature, can be transformed to an austenitic phase via heating it to around 55° C. and that it stays in a stable austenitic phase down to temperatures well below body temperature. This is very advantageous in surgical applications as devices, such as orthopaedic staples, can be programmed during manufacture with a clinical utility shape in the austentitic phase (the shape that it will take after heating during a surgical procedure) and then be deformed during manufacturing to an operable configuration in its martensitic phase (the shape in which it will be delivered to the surgeon for insertion into the body prior to heating).

Orthopaedic NiTinol staples have been available clinically in the US for approximately ten years. The manufacturers of these devices are using various instruments and power sources for heating the staples in order to effect the transformation to the austentitic phase in vivo. Tissue cautery and coagulation devices typically are available in an operating theater and are commonly used to provide heat to shape memory articles.

Shape memory materials typically have a temperature range of about 20° C. over which they make the transformation from the martensitic phase to the austentitic phase. Thus, for instance, a shape memory article designed to complete its transformation to the austentitic phase at body temperature, i.e., about 37° C., will begin transitioning at temperatures as low as 17° C., or at approximately room temperature.

Thus, shape memory articles, particularly ones designed for body temperature activation often are exposed to temperatures higher than the temperature at which they start the phase change from martensitic to austentitic phase prior to surgery, such as during transportation. Accordingly, shape memory articles often are packaged in the manufacturing plant in a constraining device that prevents them from changing shape until released from the constraining device.

Once a shape memory article has transformed to its austentitic phase, it can be transformed back to martensitic by exposing the shape memory article to a much lower temperature. In the example above, such a transition temperature back to the martensitic phase would occur at or below (minus) 15° C. thus, immediately prior to surgery, shape memory articles commonly are frozen to return them as fully as possible to their original martensitic phase and delivered to the operating room in a frozen or other cold state, such as in a cooler filled with ice.

Using a shape memory surgical staple as an example, a surgeon typically might remove the staple from its packaging and constraining device while in its martensitic phase essentially at the time it is needed for implantation. A surgeon typically might grasp the backspan of the staple with a clamp and pull it out of the constraining device. The surgeon might have an extremely small window of time in which to implant the staple into the patient, e.g., into pre-bored holes in a bone, because the staple may start its transformation from the martensitic phase to the austentitic phase almost immediately upon removal from the constraining device. Particularly, operating rooms are commonly maintained at about the austentitic phase transition starting temperature for body temperature activated shape memory articles.

Even if the operating room is colder than the activation temperature, the surgeon may have to expose the staple to body temperature for a period of time before while he is locating the holes within which the legs of the staple must be inserted, which also could cause the staple to start deforming before it is in the implantation position.

This can be a significant problem during surgery insofar as, once the staple or other shape memory article begins deforming, then its legs may not match up with the pre-bored holes into which they are to be inserted. In such situations, typically, the surgeon would have to discard the staple and start over with a new staple and move much more quickly.

SUMMARY OF THE INVENTION

The invention pertains to an apparatus for removing a shape memory article, such as a shape memory surgical staple, from its constraining device and delivering it directly to the surgical implantation site while still constraining the shape memory device from deforming until the shape memory device is implanted.

BRIEF DESCRIPTION OF THE DRAWINGS

FIGS. 4A-4F illustrate the transfer apparatus of FIG. 3 in various stages of use.

DETAILED DESCRIPTION OF THE INVENTION

As noted above, shape memory staples and other shape memory articles often are packaged in a constraining device so that they do not deform should they be exposed to temperatures higher than the phase transition starting temperature. Nevertheless, shape memory articles must spend some period of time between being removed from their constraining packaging and being fully implanted into bone, tissue, or any other anatomical feature, during which time the article may deform prematurely, which may make it difficult or impossible to implant correctly.

Figure 1:
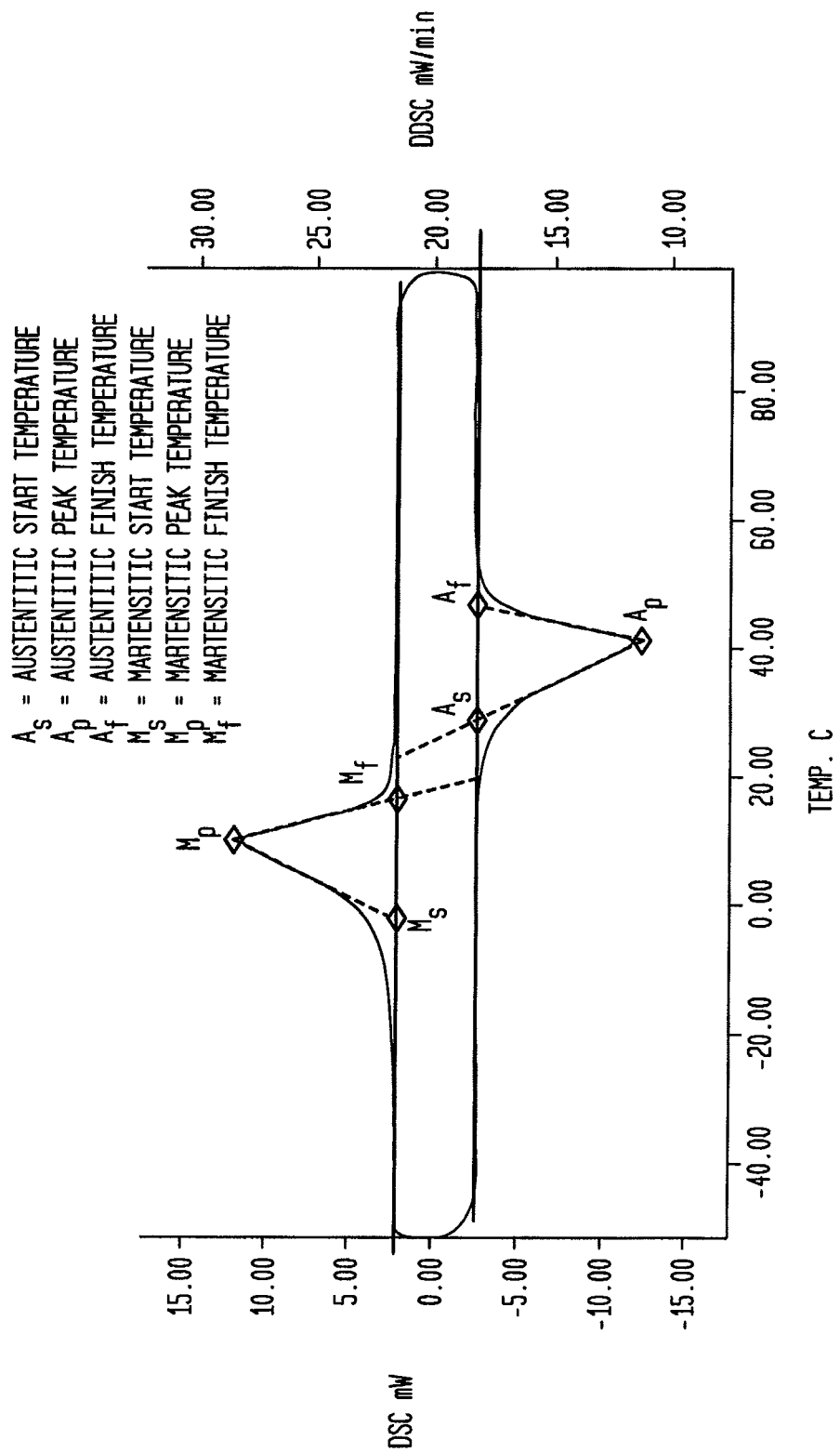
FIG. 1 is a graphical representation of a dynamic scanning calorimetry for one particular NiTinol composition
Figure 2:
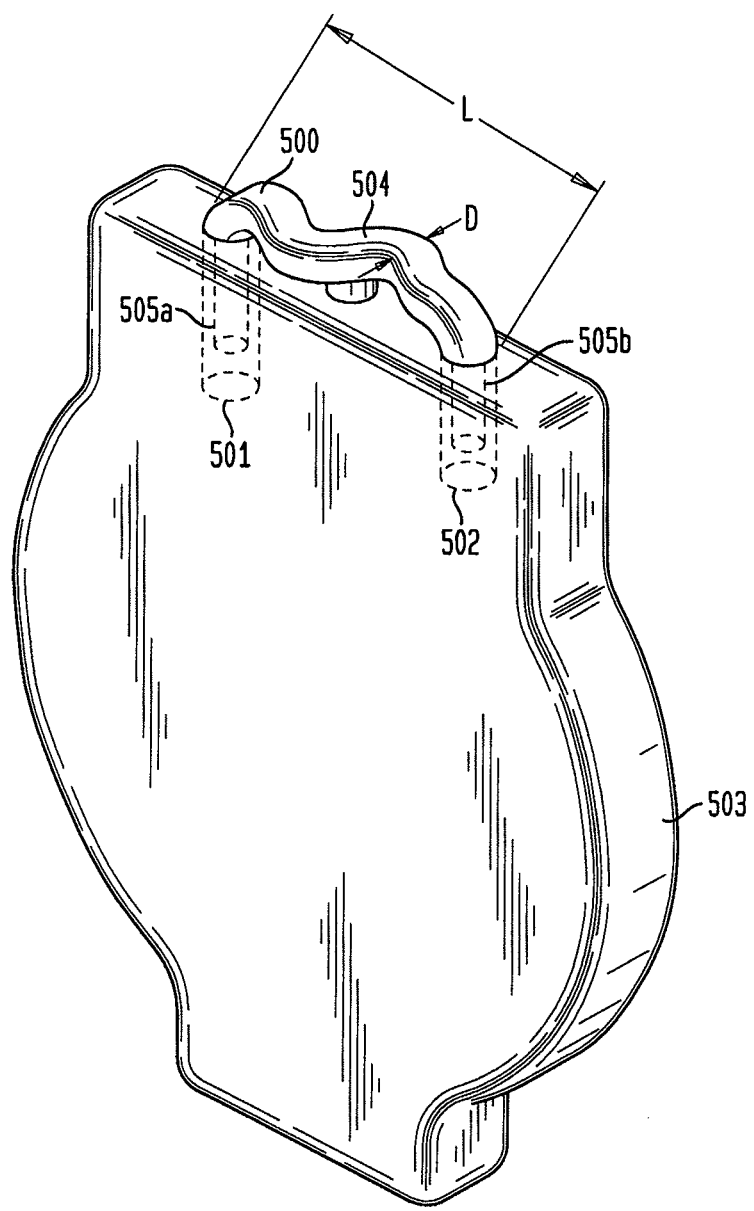
FIG. 2 is a perspective view of a shape memory surgical staple disposed in a constraining device pre-surgically.

FIG. 2 shows a shape memory staple 500 comprising a backspan 504 with legs 505a, 505b extending substantially orthogonally from the opposite ends of the backspan. The staple is disposed with its legs 505a, 505b extending into passages such as holes 501 and 502 in a constraining device 503 and with its backspan without (i.e., outside of) the constraining device 503. As long as the staple is disposed with its legs in the holes 501, 502 of the constraining device 503, it essentially cannot deform to any significant extent.

Figure 3:
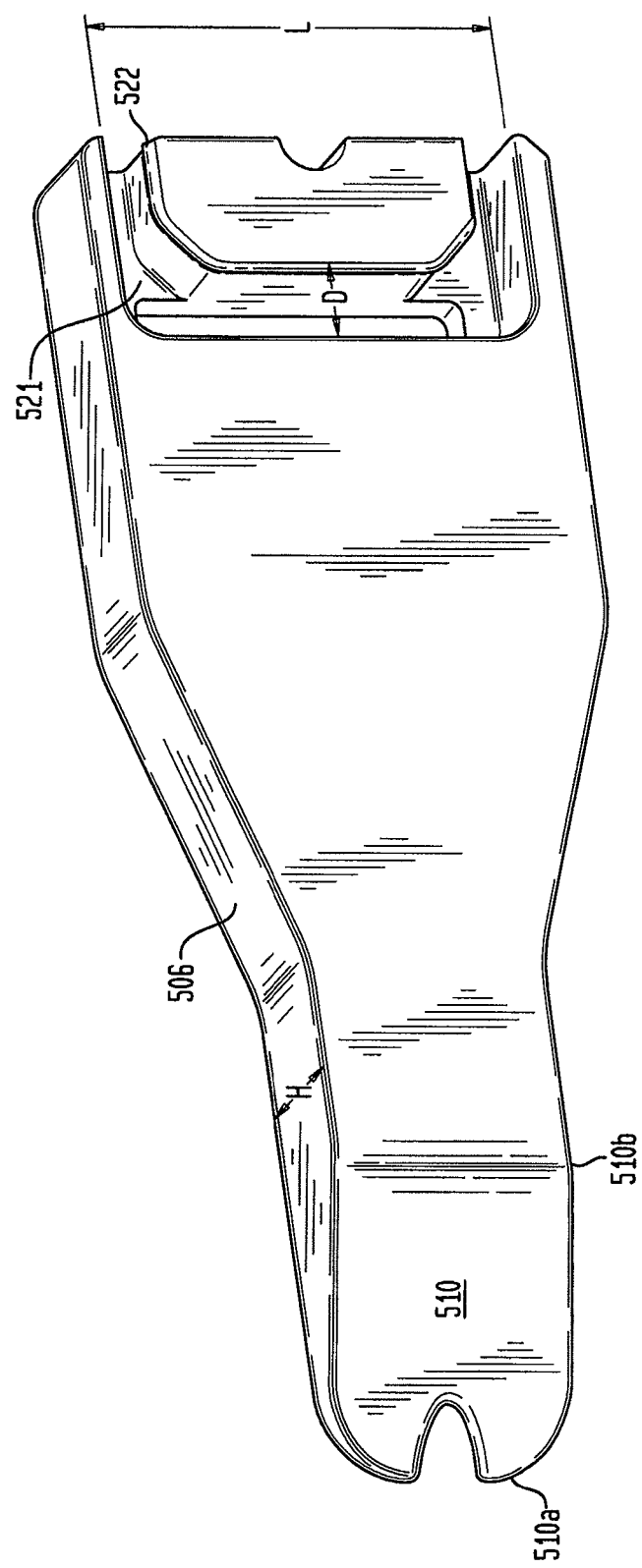
FIG. 3 is a perspective view of a transfer apparatus in accordance with the principles of the present invention.

In order to further prevent or minimize the possibility of the shape memory staple 500 (or other shape memory article) from deforming prematurely after it is removed from the constraining device 503, but before it is fully implanted, a transfer device is provided such as the exemplary transfer device 506 shown in FIG. 3. In accordance with this embodiment, the transfer device 506 includes a wedge formation 510 that provides a ramp running from a minimal height at its front end 510a and terminating at a maximum height, H, at its rear end 510b, as shown in FIG. 3. The transfer device 506 further comprises a passage such as groove 521 in a major surface 506a of the transfer device 506 having a first portion 521a that conforms to the size and shape of the backspan 504 of the staple 500 (at least in terms of the length, L, and the diameter, D, of the backspan 504) and second and third portions 521b, 521c that each conforms to a proximal portion of the legs of the staple. The ends of the second and third portions 521b, 521c of the groove are open to a second surface of the transfer device so that the distal portions of the legs of the staple may extend from the transfer device from those ends.

As will be described in detail below, the staple will be secured in the groove 521 from a time prior to removing the staple 500 from the constraining device 503 up until the staple 500 is implanted. Particularly, with reference to FIG. 4A, when a surgeon is ready to deliver the shape memory staple 500 to the implantation site, the ramp 510 of the transfer apparatus is used to partially pull the legs of the staple out of the holes in the constraining device. Particularly, as shown in FIG. 4A, the surgeon pushes the ramp 510 of the transfer apparatus 506 in the direction of arrow A between the backspan 504 of the staple 500 and the surface 503a of the constraining device 503 against which the staple backspan is abutted so as to force the backspan 504 away from the surface 503a up to the height H of the ramp. This terminal height H of the ramp may be equal to or slightly greater than the length of the leg portions of the groove 521 in the transfer apparatus.

The transfer apparatus is then pulled back out in the direction opposite of arrow A to disengage it from the staple 500 and the constraining device 503. At this point, after the ramp has been removed, the shape memory staple still essentially cannot deform from its constrained state since the ends of the legs 505a, 505b are still constrained within the holes 501, 502 of the constraining device 503. Next, the surgeon grasps the transfer apparatus 506 by the ramp portion 510 and forces the groove 521 over the backspan 504 and proximal portions of the legs 505a, 505b of the staple 500 as shown in FIG. 4B to lodge the staple 500 in the groove 521.

With reference to FIG. 3, in one embodiment of the invention, the groove 521 may have one or more detents 522 to assure that the staple 500 does not inadvertently fall out of the groove after it has been pushed into it. The detents may, for instance, be narrowed portions of the groove formed by one or more protrusions in the groove that make that portion of the groove narrower than the diameter D of the wire from which the staple is formed, which protrusions the staple must be snapped past to become seated within the groove 521.

Figure 4B:
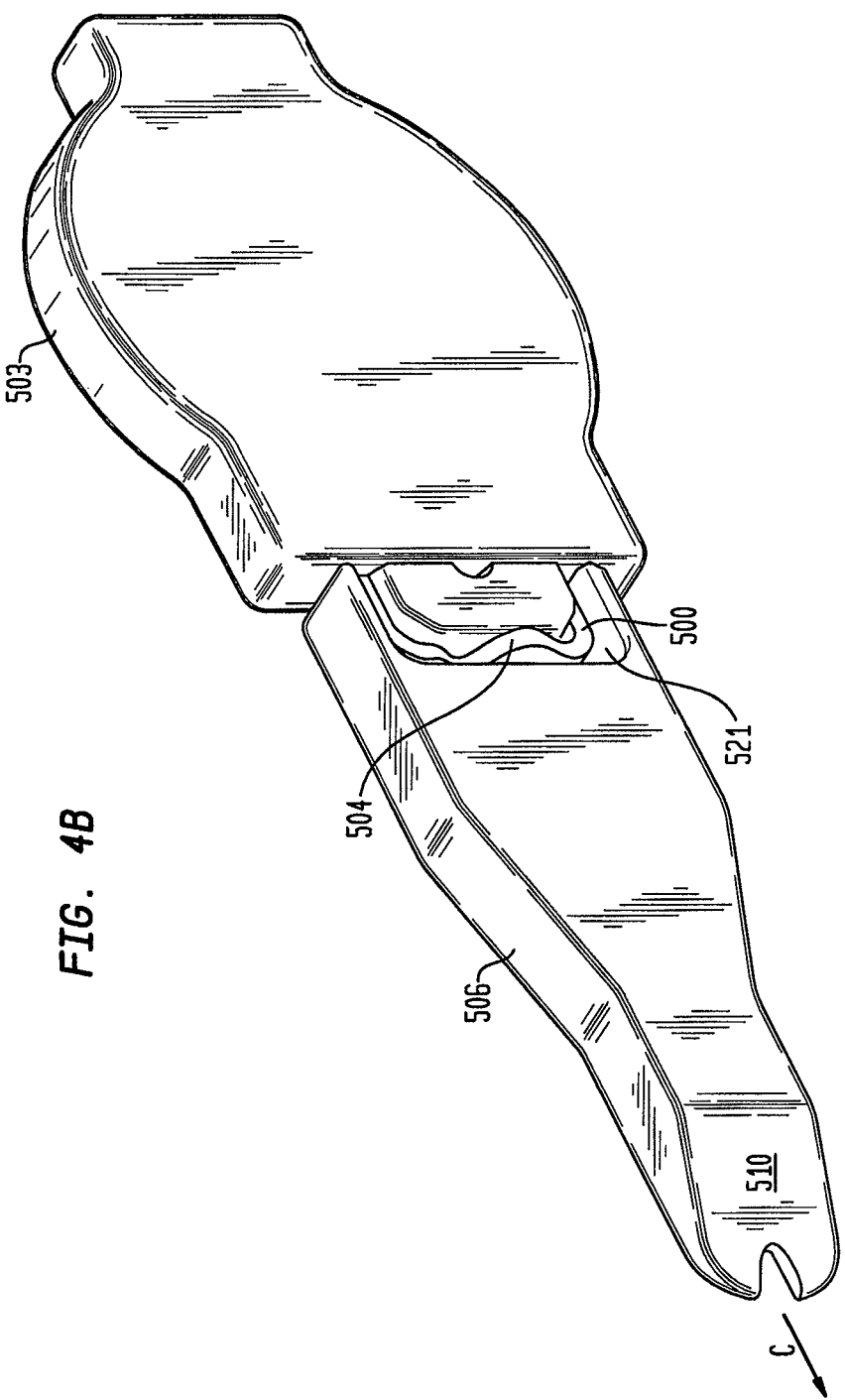
Figure 4C:
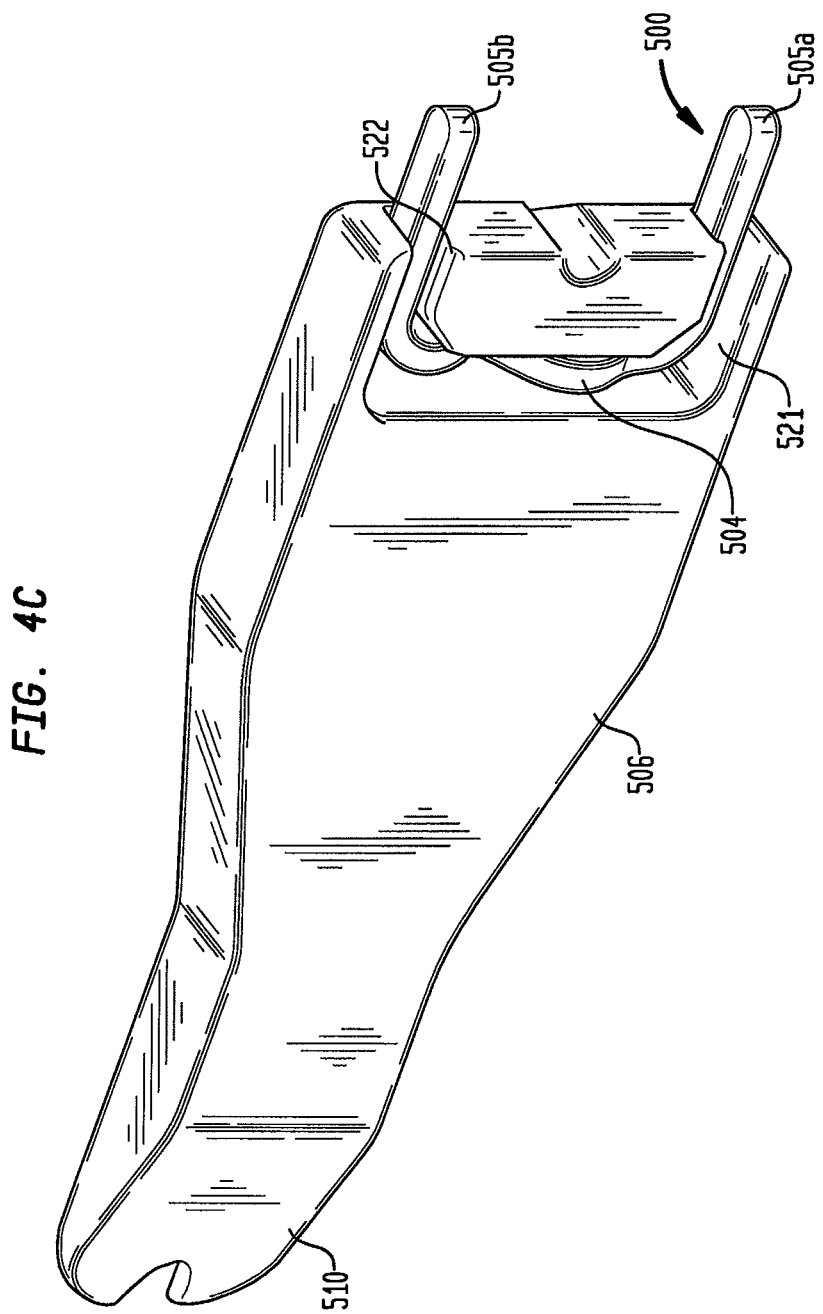

Next, with reference to FIGS. 4B and 4C, the surgeon can pull the transfer device 506 away from the constraining device 503 in the direction of arrow C (see FIG. 4B) to pull the distal ends of the staple legs 505a, 505b out and completely free of the constraining device 503 (FIG. 4C). At this point, even though the distal ends of the legs 505a, 505b of the shape memory staple 500 are free, the transfer apparatus 506 is constraining the proximal ends of the legs (as well as the backspan 504) of the staples, thus still substantially preventing the staple 500 from deforming.

The transfer apparatus 506 can then be used to hold the staple and deliver the staple to the implantation site. Only after the distal ends of the legs 505a, 505b have been inserted into the pre-bored holes at the implantation site is the staple 500 released from the transfer apparatus 506.

Figure 4D:
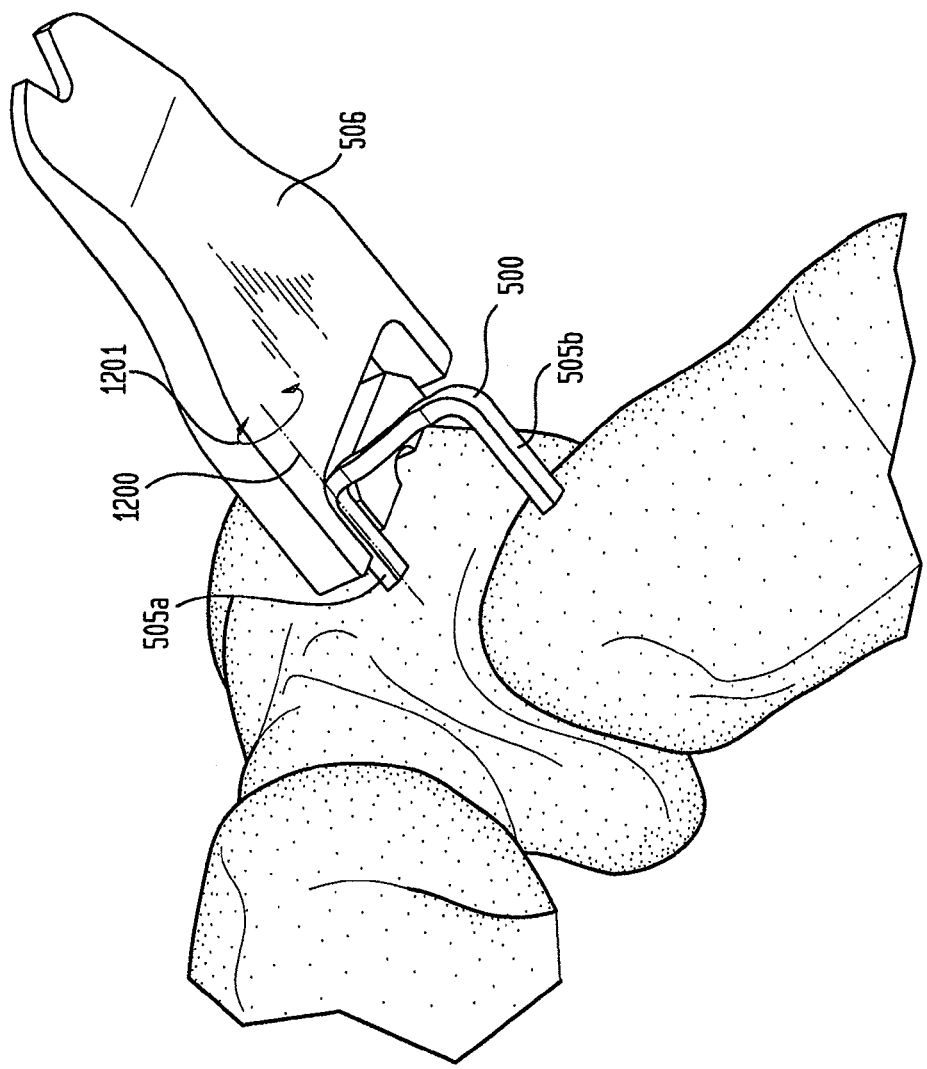

For instance, once the distal ends of the legs are reasonably firmly implanted in the holes, the staples should be relatively stable such that the transfer apparatus can release the staple without inadvertently removing the staple from the holes. If the staple is not sufficiently stable in the implantation holes, the part of the exposed portion of one of the legs of the staple 500 that is extending from the hole but not within the groove 521 of the transfer apparatus 506 can be grasped with a clamp to help stabilize it while the transfer apparatus 506 is snapped off of the staple 500. The staple can be removed from the transfer apparatus 506 by twisting it about an axis substantially parallel to the axes of the legs of the staple. For instance, the transfer apparatus 506 may first be twisted about the axis of one of the legs, e.g., leg 505a, of the staple (to snap the other leg 505b past the detent 522 and out of the transfer apparatus) as illustrated in FIG. 4D (with arrow 1201 showing the direction of twisting and axis 1200 showing the axis of twisting. Then, referring to FIG. 4E, the transfer apparatus 506 may be twisted in the opposite direction (see arrow 1205 showing the direction of twisting) about another axis 1203 substantially parallel to, but not collinear with, the axis 1202 of the first leg 505a to snap the first leg 505a past the detent 522 and out of the transfer apparatus to completely remove the staple from the transfer apparatus. At this point, the staple 500 can then be pushed fully into the holes, as needed.

Figure 4F:
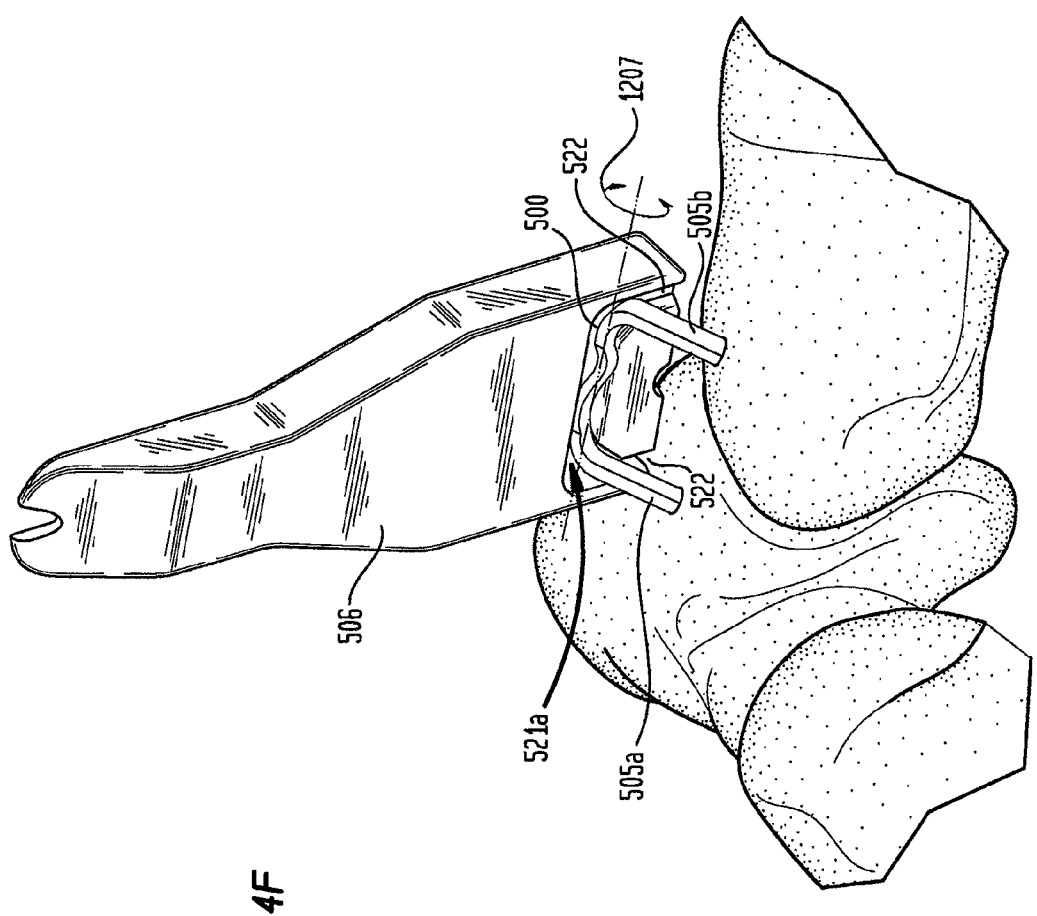
Figure 5:
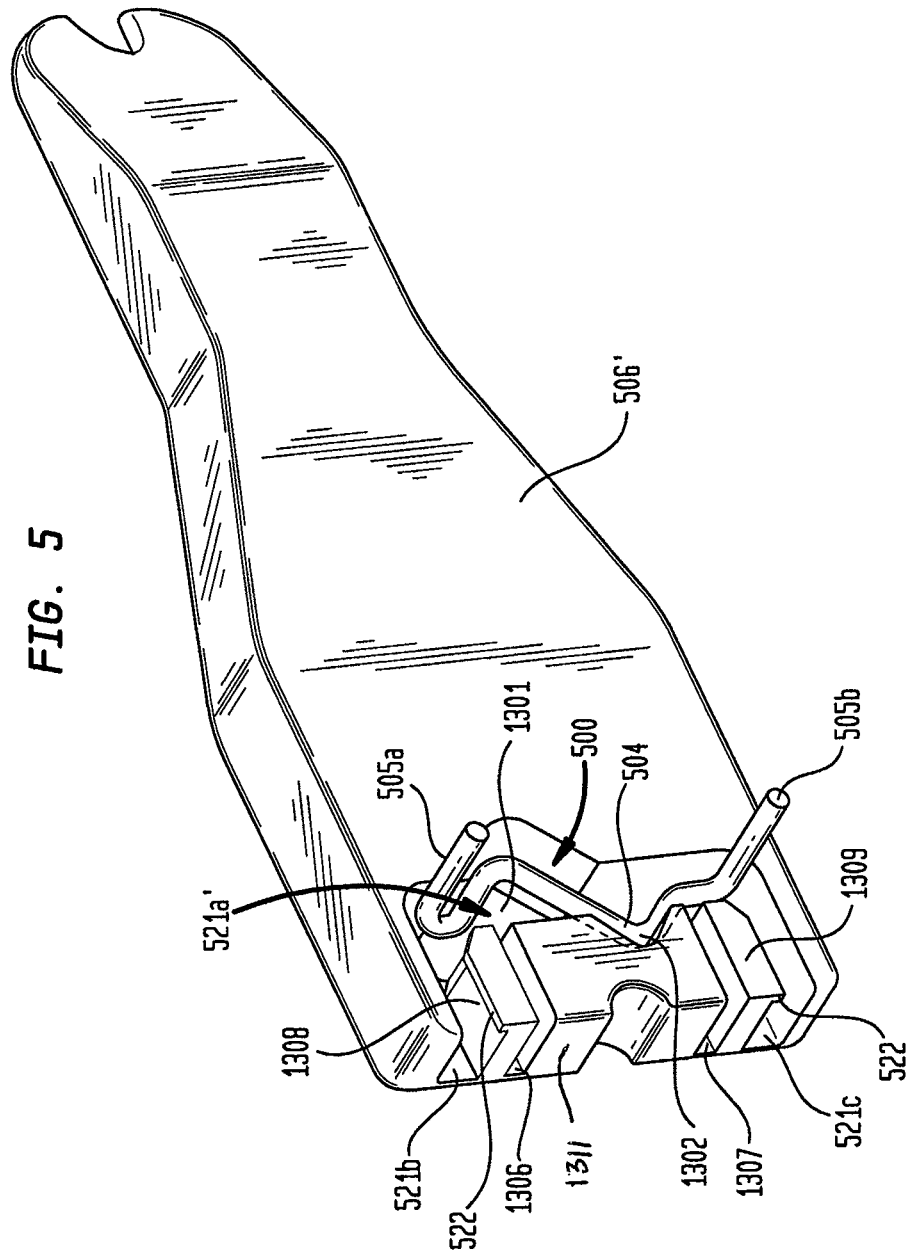
FIG. 5 is a perspective view of a transfer apparatus in accordance with another embodiment with a staple partially released therefrom.

Alternately, with reference to FIG. 4F, the transfer apparatus may be twisted about an axis 1207 generally defined by the backspan 504 of the staple as illustrated by arrow 1206 to snap both legs 505a, 505b out of the transfer apparatus simultaneously. Then, the backspan (assuming no detent adjacent the backspan) will simply fall out of the transfer apparatus. It should be noted however, that because the backspan of surgical shape memory staples typically have a zigzag in them as seen in the Figures (to allow the backspan to also achieve some compression during the transition from martensitic state to austenitic state), if the portion 521a of the channel in the transfer apparatus that accommodates the backspan is formed as a straight groove and with a width reasonably close to the diameter of the staple, there may not be enough clearance in that channel portion to permit releasing of the staple from the transfer apparatus by twisting about the backspan. Specifically, the zigzag in the backspan 504 may hit the wall of the channel portion 521a and prevent further twisting before the staple can be twisted enough to cause the legs 505a, 505b to clear the detents 522. Since a reasonably tight fit of the backspan 504 in the channel portion 521a of the transfer apparatus 500 is desirable in order to keep the staple 500 from sliding in the transfer apparatus in the direction parallel to the legs 505a, 505b of the staple 500 when seated in the transfer apparatus 506, channel portion 521a may be shaped eccentrically to accommodate the zigzag and to permit twisting of the staple about its backspan. FIG. 5 illustrates such an embodiment. As can be seen, the portion of the channel 521a' in the transfer apparatus 506' that accepts the backspan 504 of the staple has two portions 1301 and 1302 that cause that channel portion 521a' to correspond generally to the zigzag shape of the backspan of the staple. As shown, the channel portion 521a' can accommodate the backspan 504 of the staple even when the staple is twisted a full 90° out of the transfer apparatus, as shown.

FIG. 5 also illustrates another alternative feature of the transfer apparatus. Particularly, in order to enhance the ability of the transfer apparatus 500' to deform to allow the legs 505a, 505b of the staple 500 to snap past the detents 522 as previously described, grooves 1306, 1307 are cut into the material of the transfer apparatus 506' parallel to the channel portions 521b, 521c bearing the detents. This will allow more flex in the material portions 1308, 1309 adjacent these channel portions 521b, 521c. This feature may be particularly desirable in connection with transfer apparatus for larger size staples, which transfer apparatus may be larger in size, and therefore inherently more rigid.

The transfer apparatus also may be used to remove the staple from the surgical site in cases where that is necessary. Again, the wedge formation 510 may be inserted between the backspan of the staple (or other proximal portion of a shape memory article) and the bone (or other anatomical feature) to which the backspan is adjacent in order to force the backspan away from the bone essentially as described above in connection with the use of the wedge portion to pull the backspan away from the constraining device 503. Once the wedge is inserted so as to push the backspan sufficiently away from the surface, the surgeon can simply pull the transfer apparatus 506 perpendicularly away from the surface of the bone. If more force is necessary than can reasonably be applied via the transfer apparatus, then the surgeon may instead remove the transfer apparatus and grasp the staple with a grasping tool to pull it out.

The transfer apparatus comes in contact with the anatomy at the surgical site. Accordingly, it should be made of a biocompatible material, preferably a plastic biocompatible material. The transfer apparatus can be designed as a reusable device or as a single use device. If it is to be reused, it should be fabricated from a material that can withstand repeated autoclaving processes. Many such materials are well known in the medical arts.

Figure 6:
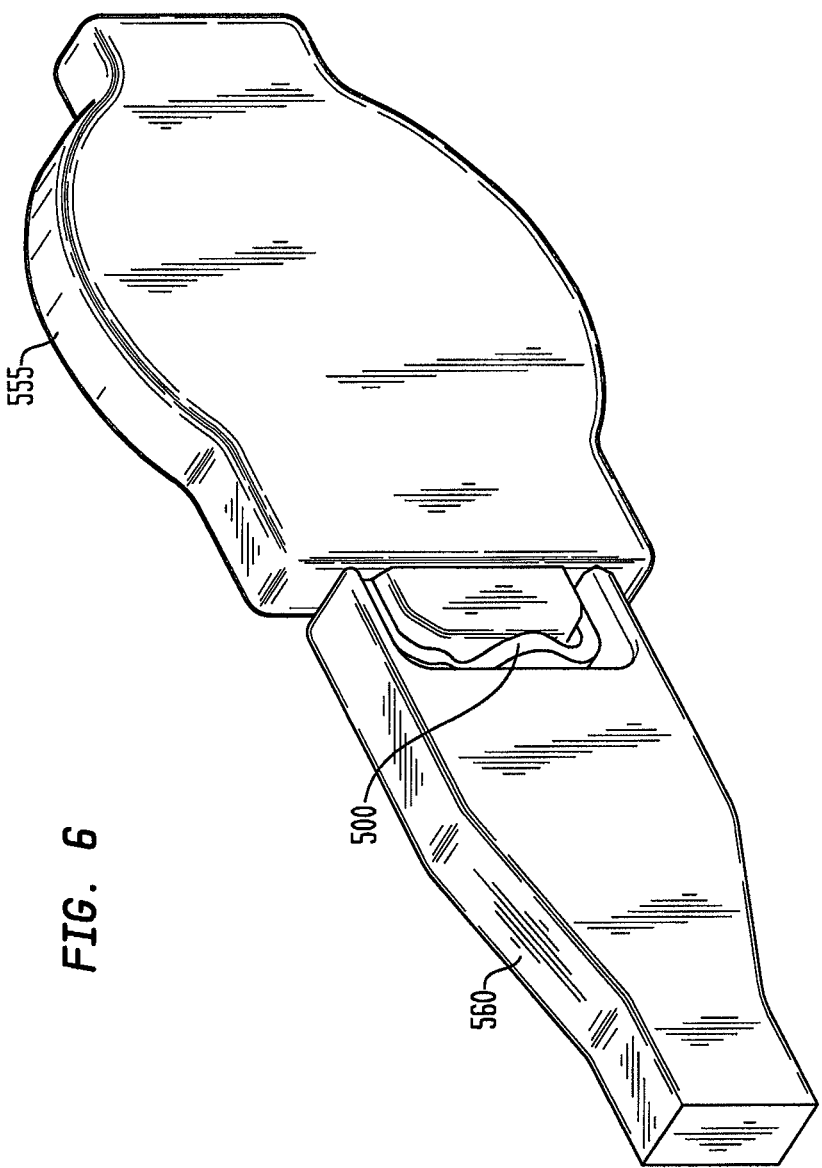
FIG. 6 is a perspective view of a shape memory surgical staple packaged pre-surgically in accordance with another embodiment of the present invention.

FIG. 6 illustrates an alternative embodiment of the invention. In this embodiment, the shape memory article 500 is packaged at the factory embedded within both a constraining device 555 and a transfer apparatus 560 as shown in FIG. 6. In this embodiment, there is no ramp on the transfer apparatus insofar as the staple backspan and the proximal portion of the legs are already embedded in the groove of the transfer apparatus.

In another embodiment, the constraining device may be completely eliminated. For instance, depending primarily on the size, shape, and shape memory properties of the shape memory device as well as the size and shape of the passage in the transfer apparatus relative to the shape memory device, the transfer apparatus may sufficiently restrain the shape memory article so as to completely eliminate the need for a separate constraining device to hold the distal end of the shape memory article pre-surgically. Accordingly, the shape memory article may simply be packaged without a constraining device essentially as shown in FIG. 4C, i.e., with the proximal end embedded in the transfer apparatus and the distal end free.

Figure 7A:
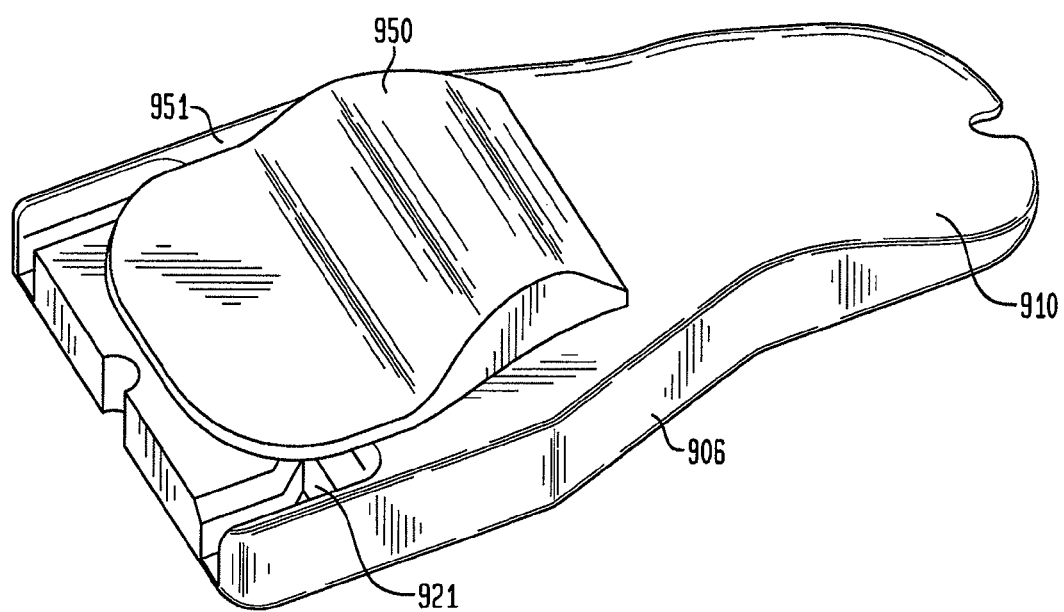
FIG. 7A is a top perspective view of an alternative embodiment of a transfer apparatus in accordance with the principles of the present invention in a closed condition.
Figure 7B:
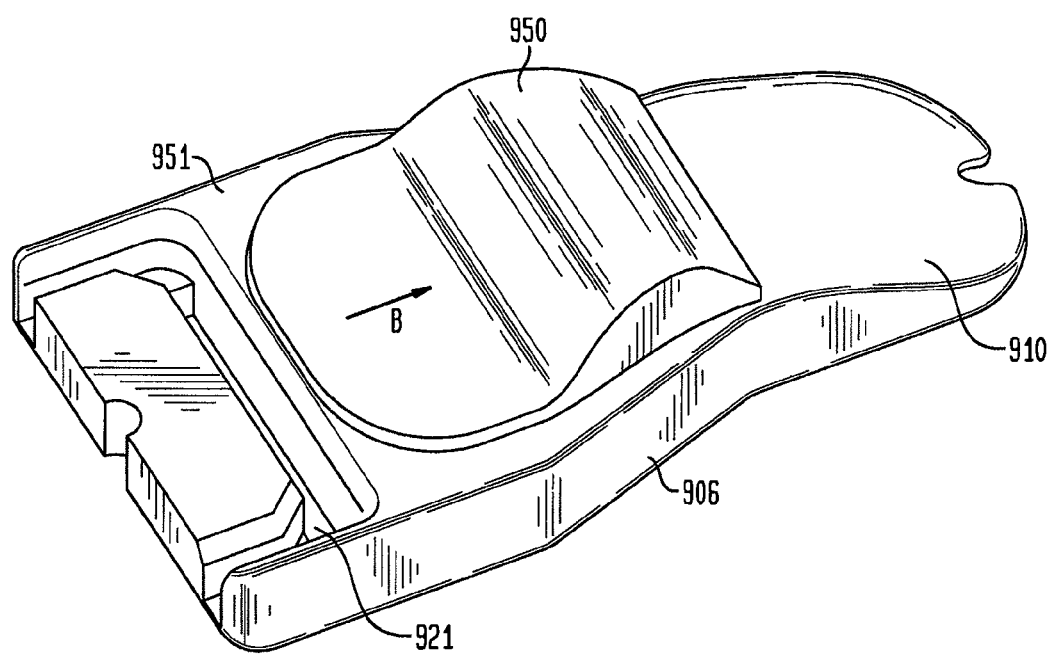
FIG. 7B is a top perspective view of the transfer apparatus of FIG. 7A in an open condition.
Figure 7C:
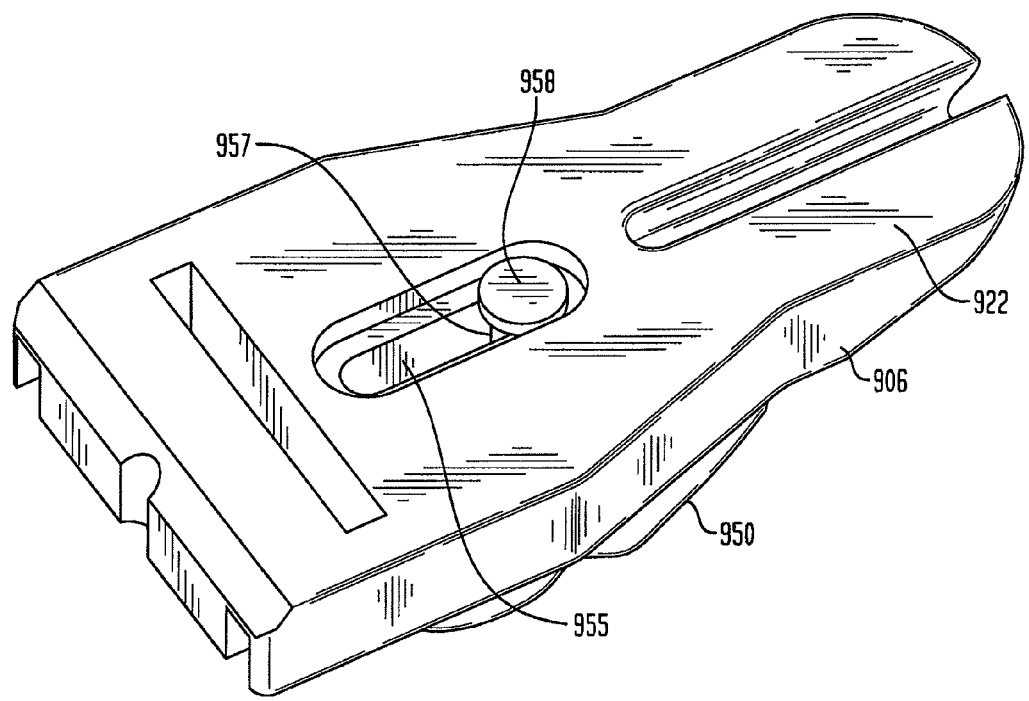
FIG. 7C is a bottom perspective view of the transfer apparatus of FIGS. 7A and 7B.

FIGS. 7A-7C illustrate another embodiment of the invention. This embodiment is substantially similar to the embodiment described above in connection with FIGS. 2-3 insofar as the transfer apparatus includes a wedge formation 910 and a groove 921 that conforms to the size and shape of the backspan of the shape memory staple and the proximal portions of the legs of the staple. However, rather than having one or more detents in the groove to assure that the staple does not inadvertently fall out of the groove, this transfer apparatus includes a cover portion 950 that is slidable between an open position, in which it does not cover the opening of the groove 921 in the major surface 951 of the transfer apparatus (the position shown in FIG. 7A) and a closed position, in which it does at least partially cover the groove 921 (the position shown in FIG. 7B). The cover 950 may be shaped, as shown, to provide a convenient thumb rest for the surgeon when holding the transfer device with a staple in it.

In this embodiment, the transfer apparatus is delivered to the surgeon with the cover 950 in the closed position, as shown in FIG. 7A. The cover would remain in this closed position throughout the entire surgical procedure until the time when the transfer apparatus is to be detached from the staple (e.g., after the distal portions of the legs of the staple have been inserted into the holes in the anatomical feature in which it will be implanted). Then, the surgeon can slide the cover 950 back with his thumb and simply translate the transfer apparatus in the direction represented by arrow B in FIG. 7B, i.e., parallel to the major surface 951, to disengage the transfer apparatus from the staple. An advantage of this embodiment is that the detents may be eliminated so that the entire groove 921 is sized slightly larger than the diameter of the staple so that no force need be applied to the staple when removing the transfer apparatus from the staple after partial implantation.

The slidable cover 950 may be attached to the main body of the transfer apparatus by any reasonable mechanism that would allow it to slide. For instance, in one embodiment illustrated in FIG. 7C, a slot 955 is provided in the aforementioned major surface 951 and completely through to the opposing major surface 922 of the transfer apparatus 906 and a corresponding pin 957 is provided on the underside of the cover 950 to mate with the slot 955 and slide in the slot. The distal-most portion of the pin 957 may be enlarged to form a button, ball, T shaped extension or other form of flange 958 with a diameter larger than the width of the slot so that the flange 957 is trapped in the slot 955 to hold the cover 950 to the main portion of the transfer apparatus, but allow it to slide in the slot 955.

In the embodiment illustrated in FIGS. 7A-7C, the cover 950 covers only the backspan portion of the groove 921. However, in other embodiments, it can cover the entire groove, including the portions that hold the proximal portions of the legs of the shape memory staple. This might provide more support for the staple and, particularly, prevent it from rocking about an axis parallel to the legs of the staple during implantation.

In another embodiment, the features of the embodiment of FIG. 5 allowing easier removal of the staple by providing grooves 1306, 1307 parallel and adjacent the channel portions 521b, 521c that allow the material portions 1308, 1309 that bear the detents 522 to flex more easily (see FIG. 5) may be combined with the cover feature of the embodiment of FIGS. 7A-7C. In fact, in yet another embodiment, the grooves 1306, 1307 may be reduced to nominal size such that there is a very small gap or no actual gap between material portions 1308, 1309 and middle material portion 1311. Instead, material portion 1311 (or at least a substantial portion of it extending up to the front surface) may be integral with or attached to the cover so that it slides back with the cover. Thus, when the cover is in the closed position covering backspan channel portion 521a, the staple is held securely in the channel by detents 522 because material portions 1308, 1209 bearing the detents cannot move because they are blocked by material portion 1311. However, when the cover is slid open to reveal the backspan channel 521a, the material portion 1311 also slides back so that it no longer blocks material portions 1308, 1309. Material portions 1308, 1309 may be slidable medially once material portion 1311 is moved away. Alternately, they may be flexible as described in connection with the embodiment of FIG. 5. Of course, in such an embodiment, material portion 1311 would need to be specially shaped and attached to the cover to provide clearance to slide back without being blocked by the backspan of the staple held in the channel portion 521a. For instance, material portion 1311 could be attached to the cover via the flange 958 adjacent the back surface 922 (as illustrated in the embodiment of FIG. 7C) and material portion could be shallower in depth so as not to extend all the way to front surface 951 so as not to interfere with the staple. Furthermore, another channel would need to be provided in the transfer apparatus into which material portion 1311 would slide when the cover is opened.

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. An apparatus for holding a shape memory article, the shape memory article comprising a proximal portion and a distal portion and adapted to be implanted into an anatomical feature with the distal portion first, the apparatus comprising:
a body extending longitudinally from a proximal end to a distal end, the body having a passage for receiving the proximal portion of the shape memory article, the passage comprising a groove on the body's outer surface that opens transversely to the body, the passage being shaped to substantially prevent the shape memory article from deforming in accordance with its shape memory properties when the proximal portion of the shape memory article is positioned in the passage.

2. The apparatus of claim 1 wherein the body is a unitary body and the passage formed in the unitary body is shaped and sized so that the distal portion of the shape memory article can be implanted into an anatomical feature while the shape memory article is positioned in the passage of the apparatus.

3. A combination comprising the apparatus of claim 2 and the shape memory article.

4. The combination of claim 3 wherein the shape memory article is a medical staple and wherein the proximal portion of the staple comprises a backspan and proximal portions of legs extending from the backspan, and the distal portion of the staple comprises distal portions of the legs.

5. The combination of claim 3 wherein the body has a lateral surface extending from the proximal end to the distal end, the passage comprising a first groove open to a lateral surface of the body.

6. The combination of claim 5 wherein the first groove comprises at least a portion bearing a detent adapted to hold the shape memory article in the groove.

7. The combination of claim 6 wherein the detent comprises an overhang defining a clearance that is less than a diameter of a section of the proximal portion of the shape memory article.

8. The combination of claim 6 further comprising a second groove in the apparatus positioned and shaped to enhance flexibility of a portion of the apparatus adjacent to a portion of the first groove bearing the detent for permitting the shape memory article to be forced past the detent as the enhanced-flexibility portion of the apparatus is deflected into the second groove.

9. The combination of claim 5 wherein the first groove comprises a first portion adapted to receive a backspan of a shape memory staple and second and third portions adapted to receive proximal portions of first and second legs of the medical staple, respectively.

10. The apparatus of claim 1 further comprising a cover movable on the body between a closed position in which the cover covers at least a portion of the passage so as to prevent a shape memory article positioned in the passage from being removed from the passage and a second position in which the cover does not cover the passage so that a shape memory article positioned in the passage can be removed from the passage.

11. The apparatus of claim 10 wherein the cover is slidably attached to the body.

12. A combination comprising the apparatus of claim 11 and the shape memory article, wherein the shape memory article is a medical staple and wherein the proximal portion of the staple comprises a backspan and proximal portions of legs extending from the backspan, and the distal portion of the staple comprises distal portion of the legs and wherein the passage comprises a groove on a surface of the apparatus and wherein the cover covers the surface of the apparatus above the groove when in the closed position and does not cover the surface of the apparatus above the groove when in the closed position.

13. The combination of claim 12 wherein the groove comprises a first portion adapted to receive a backspan of the shape memory staple and second and third portions adapted to receive proximal portions of first and second legs of the medical staple, respectively, the first portion of the groove being shaped to provide a clearance space for accommodating a zigzag shaped backspan of the staple during twisting of the staple about an axis generally parallel to the backspan.

14. A combination of the apparatus and shape memory article of claim 3 in further combination with a constraining device, the constraining device comprising a passage sized and shaped to receive the distal portion of the shape memory article so as to substantially prevent the distal portion of the shape memory article from deforming.

15. The combination of claim 14 wherein the apparatus comprises a first surface from which the distal portion of the shape memory article will extend when the proximal portion of the shape memory article is positioned in the passage in the apparatus, and the constraining device comprises a second surface from which the proximal portion of the shape memory article will extend when the distal portion of the shape memory article is positioned in the passage in the constraining device.

16. The combination of claim 15 wherein the first surface of the apparatus and the second surface of the constraining device abut when the proximal portion of the shape memory article is positioned in the apparatus and the distal portion of the shape memory article is positioned in the passage of the constraining device.

17. The combination of claim 15 wherein the shape memory article comprises a medical staple having a backspan and first and second legs extending from the backspan, the first and second legs having proximal portions adjacent to the backspan and distal portions and wherein the passage in the constraining device comprises two bores positioned, sized, and shaped to receive the distal ends of the first and second legs of the medical staple.

18. The apparatus of claim 1, the body further comprising a first surface from which the distal portion of the shape memory article will extend when the proximal portion of the shape memory article is positioned in the passage in the apparatus and a grasping portion extending away from the passage in a direction opposite from the direction of extension of the distal portion of the shape memory article.

19. The apparatus of claim 1, the body further comprising a ramp portion having a height that varies along its length.

20. The apparatus of claim 19 wherein the passage defines a depth of the shape memory article that must be exposed in order for the shape memory article to be received in the passage and wherein the ramp portion has a maximum height substantially equal to the depth.

21. The apparatus of claim 19 wherein the shape memory article comprises a medical staple having a backspan and first and second legs extending from the backspan, the first and second legs having proximal portions adjacent to the backspan and distal portions and wherein the ramp portion has a maximum height and wherein the passage in the apparatus is adapted to receive the backspan and the proximal portions of the legs of the medical staple and wherein the passage in the apparatus comprises a groove in a first surface of the apparatus, the groove comprising a first portion adapted to receive the backspan of the medical staple and second and third portions adapted to receive the proximal portions of the first and second legs of the medical staple, the second and third portions of the groove each having a length and extending and open to a second surface of the apparatus from which the distal portions of the legs of the medical staple will extend when the maximal portion of the medical staple is positioned within the passage and wherein the length of the second and third portions of the groove is substantially equal to the maximum height of the ramp.

22. An apparatus for holding a shape memory article, the shape memory article comprising a proximal portion and a distal portion and adapted to be implanted into an anatomical feature with the distal portion first, the apparatus comprising:

an elongated body having a first major surface, a second major surface opposite the first major surface, and a thin peripheral edge between the first and second major surfaces, the body defining a passage open to one of the first and second major surfaces of the body, the passage being configured for receiving the proximal portion of the shape memory article, the passage being shaped to substantially prevent the shape memory article from deforming in accordance with its shape memory properties when the proximal portion of the shape memory article is positioned in the passage.

23. An apparatus for holding a shape memory article, the shape memory article comprising a proximal portion and a distal portion and adapted to be implanted into an anatomical feature with the distal portion first, the apparatus comprising:

an elongated body having a groove in a lateral surface thereof that defines a passage for receiving the proximal portion of the shape memory article, the passage being shaped to substantially prevent the shape memory article from deforming in accordance with its shape memory properties when the proximal portion of the shape memory article is positioned in the passage; the passage comprising a first portion adapted to receive a backspan of a shape memory staple and second and third portions adapted to receive proximal portions of first and second legs of the staple, respectively.

* * * * *